United States Patent [19]

Stone et al.

[11] Plant 4,545

[45] Jun. 10, 1980

[54] SPATHIPHYLLUM NAMED BURTONI

[76] Inventors: Felix Stone, 819 Lytle St., West Palm Beach, Fla. 33405; Richard I. Slaton, 1419 Beta Ct., West Palm Beach, Fla. 33406

[21] Appl. No.: 17,497

[22] Filed: Mar. 5, 1979

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—Alfred H. Rosen

[57] ABSTRACT

A cultivar of Spathiphyllum characterized by foliage which is green and cream-to-white in color.

2 Drawing Figures

BACKGROUND OF THE INVENTION

Spathiphyllum plants are a genus of Araceae (Aroid family). Araceae are characterized by inflorescence composed of densely flowered spadix, and subtended by a spathe or bract often colored and showy. In the genus Spathiphyllum, the foliage of all known species is green, as is illustrated for example in the reference "Exotica 3", Century Edition 1970, Pages 232, 233 and 1719, published by Roehrs Company, E. Rutherford, N.J. 07073. In particular Spathiphyllum "Mauna Loa", the parent plant, has dark glossy green foliage.

GENERAL DESCRIPTION OF THE INVENTION

The invention is a distinct and new variety of Spathiphyllum with leaves that are cream and green colored. The leaves are also oblong or lanceolate, accuminate or cuspidate; midrib strong. The spathe is leafe like, membranceous, oblong, or lanceolate as in the parent plant. We have given the name "*Spathiphyllum burtoni*" to this new variety.

BACKGROUND OF THE NEW PLANT

Our new variety of Spathiphyllum plant originated as a mutation from Spathiphyllum "Mauna Loa", a specus which is sexually reproducible, having solid green foliage. About ten years ago, we purchased approximately 500 divisions of Spathiphyllum "Mauna Loa" which were planted as individual plants in our nursery in Lantana, Fla. The plants that grew from these divisions all had solid green leaves. After about three years, the stock on hand, which was then approximately 10,000 plants, was allowed to flower and go to seed. Some of that seed was sown for seedling plants, all of which had solid green leaves. About three years ago, one of these old stock plants mutated, and put forth in succession several leaves which were green and cream-to-white in color. We noticed this and recognized it as a new variety of the plant. This plant also produced seeds which we sowed, and the resulting plants reverted to solid green leaves. About one year ago we cut the top off, i.e. "topped", this mutated old stock plant and planted the top for more stock. A little later, we transferred the original mutated plant to a pot, and set it aside in a greenhouse in our nursery, where we observed that the plant re-grew the mutated foliage. New growth from the cane produced several leaves which were green and cream-to-white colored on the original plant. The original top, which we planted in soil similar to the soil in which the old stock was growing, grew into a plant which continues to produce leaves which are partially green and partially cream-to-white in color.

DESCRIPTION OF THE DRAWING

Our new Spathiphyllum plant is illustrated by the accompanying photographic drawing which shows our new plant foliage in full color, the showing being of both plants with leaves in full bloom and the color rendition being as nearly true as it is reasonably possible to obtain by conventional professional photographic procedures. The drawing has two figures, in which.

DESCRIPTION OF THE NEW PLANT

The following is a detailed description of our new variety of Spathiphyllum plant:

THE PLANT

Origin: Cutting or division.

Parentage: Spathiphyllum "Mauna Loa" (unpatented).

Classification:

*Botanic.*—Spathiphyllum.

*Commercial.*—*Spathiphyllum burtoni.*

*Form.*—Same as parent.

THE FOLIAGE

Referring to the accompanying photographic drawing, the plant illustrated in FIG. 1 has three variegated leaves as follows:

1. Variegated green and cream-to-white;
2. Solid patches of green and cream-to-white; and
3. Solid cream-to-white color.

The plant illustrated in FIG. 2 has two variegated leaves, as follows:

1. Variegated green and cream-to-white; and
2. Solid patches of green and cream-to-white.

Figure 1:
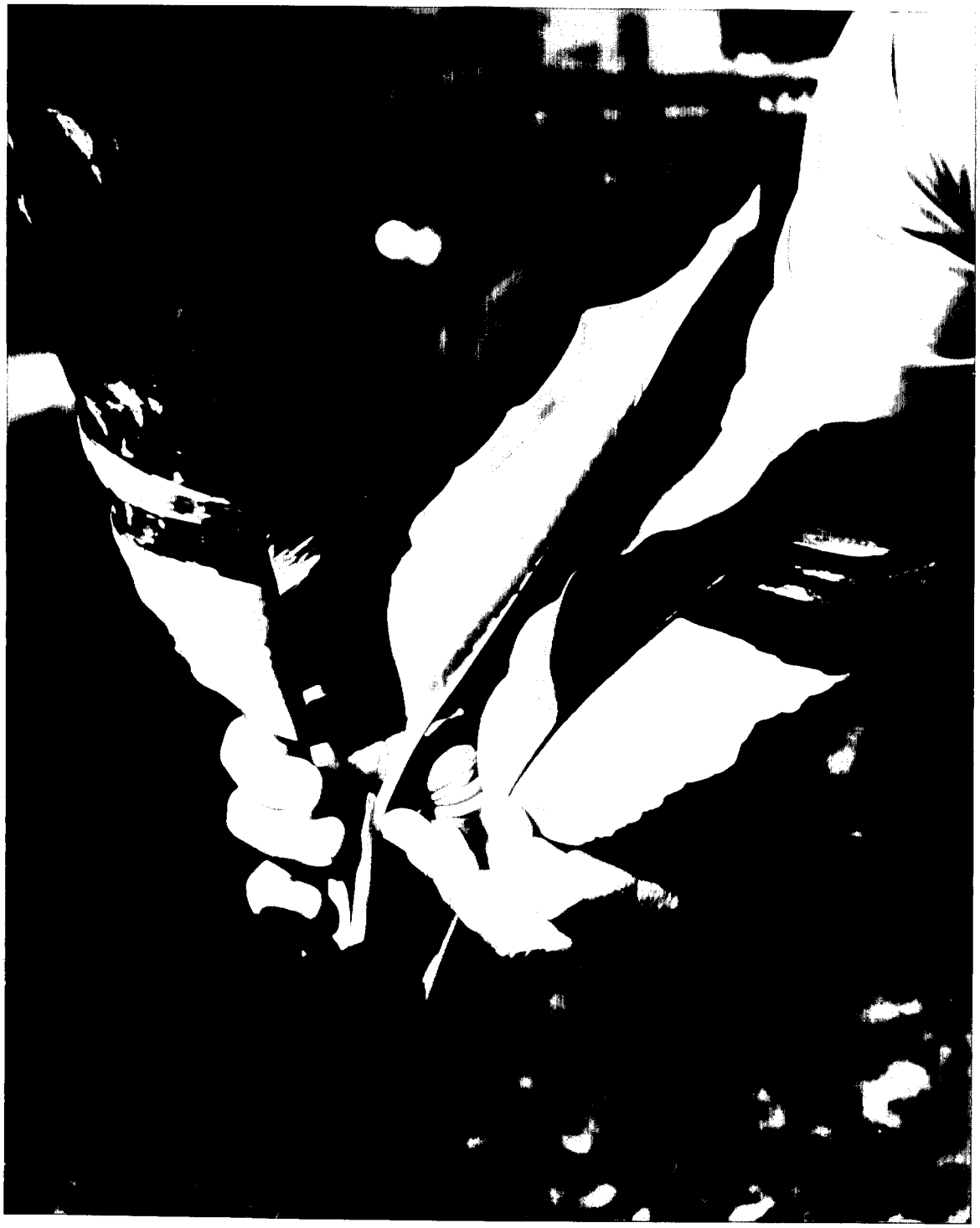
FIG. 1 shows the potted plant having second generation foliage growth on the original plant.

In the cream-to-white range of colors, the cream color shown in FIG. 1 is closely similar to the color block labelled "Code No. 1" in the Horticultural Color Guide at page 37 in "Exotica 3", in some instances shading toward a pale green that is similar to the color block labelled "Code No. 71" between the green patch and the cream colored patch. In FIG. 2, the cream-to-white color closely approaches stark white. Each plant has also a few leaves which are solid green.

Figure 2:
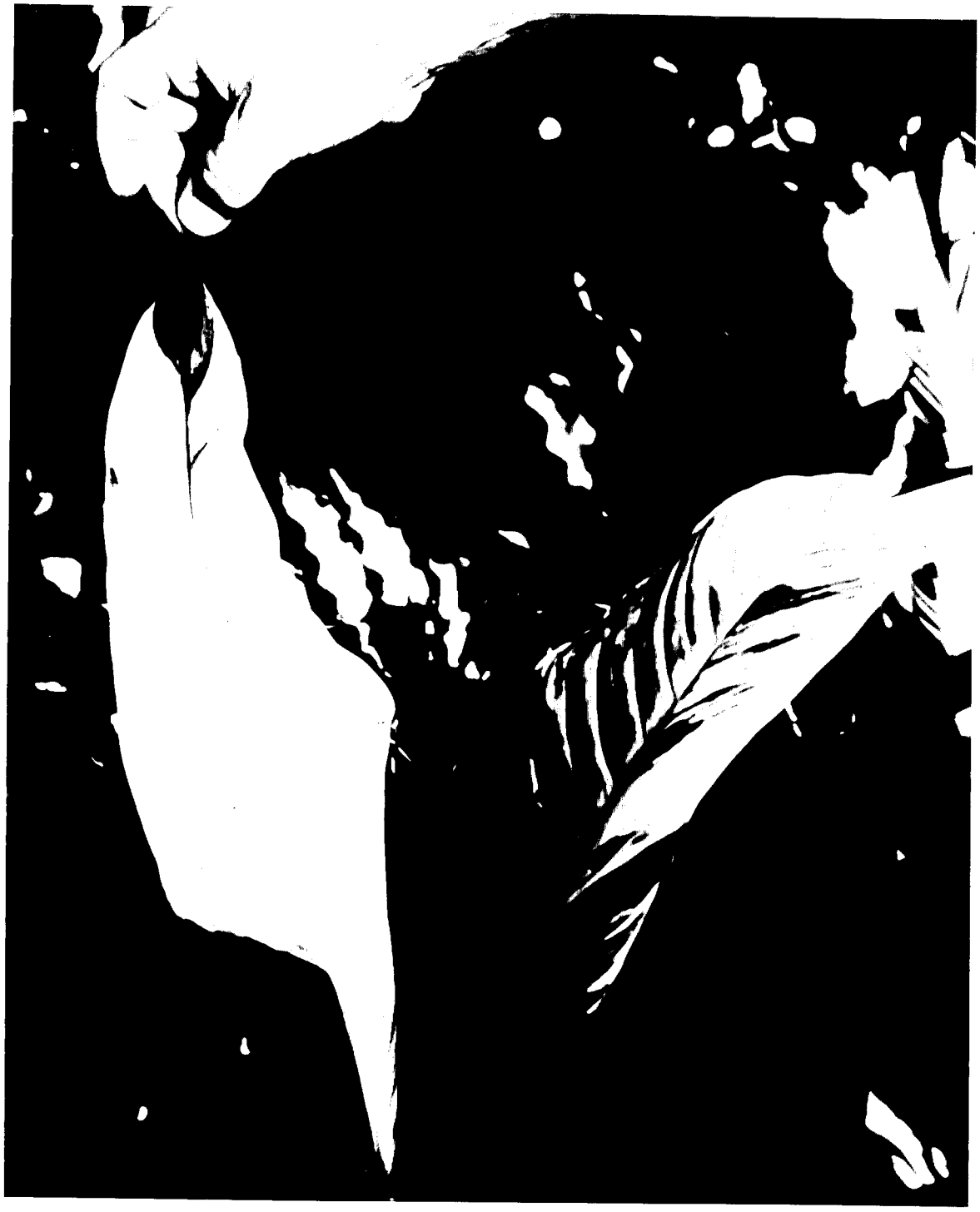
FIG. 2 shows the foliage which grew from the replanted top of the original plant.

In FIG. 2 the two variegated leaves that are shown are actually two divisions of the parent plant, and each division has separately flowered subsequent to taking the photograph.

We claim:

1. A new and distinct cultivar of Spathiphyllum, substantially as herein shown and described, characterized by foliage which is variegated from a mixture of green and cream-to-white to a substantially solid cream-to-white color.

* * * * *